United States Patent [19]

Coughlin et al.

[11] Patent Number: 4,966,999
[45] Date of Patent: Oct. 30, 1990

[54] RADIOHALOGENATED COMPOUNDS FOR SITE SPECIFIC LABELING

[75] Inventors: Daniel J. Coughlin, Robbinsville; Benjamin A. Belinka, Kendal Park, both of N.J.; Vernon L. Alvarez, Morrisville, Pa.

[73] Assignee: Cytogen Corporation, N.J.

[21] Appl. No.: 203,793

[22] Filed: Jun. 7, 1988

[51] Int. Cl.$^5$ .................. C07C 109/10; A61K 49/02; A61K 39/395
[52] U.S. Cl. ..................... 564/150; 564/390; 424/1.1; 424/85.91; 530/391; 530/405
[58] Field of Search ................... 424/1.1, 85.91; 530/388, 405, 391; 564/150, 300, 310, 311, 390

[56] References Cited

U.S. PATENT DOCUMENTS

| | | | |
|---|---|---|---|
| 2,808,416 | 10/1957 | Bell et al. | 564/150 X |
| 3,809,721 | 5/1974 | Schultz et al. | 564/390 |
| 3,933,869 | 1/1976 | Schulze . | |
| 4,430,319 | 3/1984 | Blau et al. | 424/1.1 |
| 4,450,149 | 5/1984 | Kabalka . | |
| 4,474,746 | 10/1984 | Blau et al. . | |
| 4,764,598 | 8/1988 | Srivastava et al. . | |

OTHER PUBLICATIONS

European Patent Application No. 86,303,757.8 to Wilbur, et al.
Wilbur et al., J. Labelled Compd. Radiopharm. 23 (10-12): 1304-1306 (1986).
Wilbur et al., Nucl. Med. 27(6):959 (1986).
Hadley et al., J. Nucl. Med 28 (4 Suppl.): 725 (1987).
Gersehngorn et al., in The Throid Gland: 81-121 (M. De Visscher ed. 1980).
Powe, Hybridoma 5 (Suppl. 1): 539-542 (1986).

*Primary Examiner*—John S. Maples
*Attorney, Agent, or Firm*—Pennie & Edmonds

[57] ABSTRACT

Radiohalogenated compounds which are useful as intermediates for preparing radiohalogenated antibody conjugates in which the radiohalogenated compound is site specifically attached to an oxidized carbohydrate moiety of an antibody or antibody fragment are disclosed. Methods for making the compounds and the antibody conjugates as well as methods of use of the same are also disclosed In particular, phenolic hydrazide and phenolic amine compounds are disclosed.

4 Claims, 5 Drawing Sheets

RADIOHALOGENATED COMPOUNDS FOR SITE SPECIFIC LABELING

FIELD OF THE INVENTION

The present invention relates to radiohalogenated compounds which are useful for site specific labeling of glycoprotein compositions. More particularly, the invention is directed to radiohalogenated compounds which are used as intermediates for preparing radioactive glycoprotein conjugates, including monoclonal and polyclonal antibodies and fragments thereof, in which the radiolabel is site specifically attached to an oxidized carbohydrate moiety of the glycoprotein. Also encompassed are the glycoprotein conjugates formed and methods of use of the conjugates.

BACKGROUND OF THE INVENTION

Radiohalogens such as radioactive isotopes of iodine, bromine, fluorine and astatine are useful for a variety of diagnostic and therapeutic applications. In order to enhance the delivery of the diagnostically or therapeutically effective radiohalogen to a desired target site, in vivo or in vitro, the radiohalogen is often coupled to a protein, particularly a glycoprotein such as an antibody or antibody fragment which has specific avidity or affinity for the desired target site. Unfortunately, with the radiohalogenated conjugates developed to date, there has been no method for effectively maintaining the antibody's ability to specifically localize at a target site in vivo and avoid delivery to non-target sites while at the same avoiding dehalogenation of the conjugate with undesirable localization of the free radiohalogen at non-target sites including especially the thyroid.

Direct radiohalogenation of glycoproteins particularly antibodies or antibody fragments has been unsatisfactory because the oxidizing reaction conditions required for direct radiohalogenation are particularly harmful and tend to destroy the immunospecificity of the antibody molecule. Indeed, some antibodies cannot be directly radiohalogenated without substantially destroying the antigen binding ability of the antibody (Powe, 1986, Hybridoma 5 (Suppl. 1):S39-S42). Moreover, even if the antibody activity or ability to bind antigen is maintained to an appreciable extent, directly radiohalogenated antibodies are unsuited for in vivo applications because the halogenation occurs primarily on tyrosinyl residues of the protein moiety of the antibody. The radiohalogenated tyrosinyl residues are particularly unsuitable because of the susceptibility of such structures to dehalogenation enzymes present in vivo such as the deiodinase enzymes which catabolize thyroid hormones such as thyroxine. (See generally, Gershengorn et al., 1980, in The Thyroid Gland, M. DeVisscher, ed., New York, Raven Press, p.81).

In order to avoid the problems associated with direct radiohalogenation of antibody molecules, small molecules such as the Bolten-Hunter reagent, N-succinidyl-3-(4-hydroxyphenyl-propionate and the Wood's reagent, methyl-4-hydroxybenzimidate have been radioiodinated and then coupled to an antibody molecule under comparatively mild coupling conditions. These molecules, however, have a radioiodine moiety "ortho" to a hydroxy group on an aromatic ring (herein called "ortho halogen") and consequently suffer from similar susceptibility to in vivo deiodinase enzymes as do the radioiodinated tyrosine residues of directly radioiodinated antibodies.

European Patent Application No. 86303757.8 published Dec. 3, 1986 describes a method for radiohalogenation of an antibody molecule using an aromatic ring which does not contain a hydroxy functionality and which is substituted in a para or meta position. The method requires the following steps: (1) metalation of a haloaryl compound with an organmetallic group selected from Sn(n-Bu)$_3$ and SnMe$_3$; (2) transmetalation in a site-specific reaction of the resulting aryltin compound by a group selected from HgX$_2$, Hg(OAc)$_2$, BX$_3$ or BZ$_3$ in which X is Cl, Br or I and Z is alkyl or alkoxy; (3) subsequent radiohalogenation of the metalated compound by a demetalation reaction; and (4) addition of a functional group for conjugation to a protein, preferably prior to the radiohalogenation (See also, Wilbur et al., 1986, J. Labelled Compounds and Radiopharmaceuticals XXIII (10-12):1304-06).

Unlike the method and compositions of European Patent Application No. 86303757.8, the compositions of the present invention encompass radiohalogenated aromatic compounds comprising an aromatic ring activated by an hydroxy, alkoxy or hydroxyalkoxy moiety which are formed by a rapid, easy method using starting materials which are more readily available from commercial sources. Additionally, the present method avoids cumbersome metalation of the aromatic moiety. Thus the present method avoids the need for purification steps to remove any residual or unreacted metal such as Hg which could present a problem when the products are administered in vivo. The hydroxy, alkoxy or hydroxyalkoxy moiety may enhance the aqueous solubility of the present radiohalogen intermediates. The present compositions further comprise a reactive amine moiety for site-specific attachment to an oxidized carbohydrate moiety of an antibody which is not part of nor directly involved with the antigen binding region of the antibody molecule. Thus, the present compositions and methods are particularly well suited for in vivo targeted delivery of a radiohalogen moiety that is therapeutically or diagnostically effective. The present methods and compositions are intended and will satisfy a long-felt need for easy, efficient methods and compositions of radiohalogenated products that selectively localize at a target site in vivo; are not localized at non-target sites; and do not readily release radiohalogen when administered in vivo.

SUMMARY OF THE INVENTION

The present invention provides radiohalogenated aromatic compounds in which an aromatic ring activated by a hydroxy, alkoxy or hydroxyalkoxy moiety is substituted with a radiohalogen in a para position to the activating moiety. The aromatic compounds from which the radiohalogenated compounds of the invention are derived have a blocking group, such as an alkyl, hydroxyalkyl, ester, alkyl ester, an alkyl moiety substituted with a leaving group such as chloride, bromide, tosylate, etc. group, or an alkyl moiety substituted with a primary or a secondary amino group, located ortho to the activating moiety so that when a radiohalogen group is substituted it is not at the "ortho" position. The present compounds further comprise a reactive amine group which is available for reaction with an oxidized carbohydrate moiety of an antibody or antibody fragment to form a clinically useful site-specifically attached radiohalogenated antibody conjugate.

The radiohalogenated compounds of the invention are compounds of the formula:

in which
R¹ = H alkyl or hydroxyalkyl;
R² = acid hydrazide, alkyl acid hyrazide, hydrazino, alkylhydrazine, alkylphenylhydrazine, alkylamine or alkoxyamine;
R³ = H, alkyl or R²;
R⁴ = alkyl, hydroxyalkyl or R²; and
*X = a radioactive isotope of iodine, bromine, fluorine or astatine.

The radiohalogenated compounds of the invention are useful as intermediates for preparing radioactive glycoprotein conjugates, including conjugates of monoclonal and polyclonal antibodies, in which the radiohalogen is site specifically attached via a covalent bond to an oxidized carbohydrate moiety of the glycoprotein molecule.

The present invention further provides radiohalogenated compositions comprising antibody conjugates and methods for preparing the conjugates employing the radiohalogenated compounds of the invention. The conjugates retain substantially the same immunospecificity at the unconjugated antibody or antibody fragment. These methods and compositions provide easy, efficient methods and compositions for radiohalogenated antibody conjugates that selectively localize at a target site in vivo; are not localized at non-target sites; and do not readily release free radiohalogen when administered in vivo.

The present invention further provides methods for preparing the antibody conjugates as well as methods for use of the conjugates for a number of in vivo therapeutic and diagnostic applications.

BRIEF DESCRIPTION OF THE FIGURES

The present invention may be more fully understood by reference to the detailed description, experimental examples and to the attached figures in which:

FIG. 4 (A and B) represents the biodistribution, expressed as the radioiodinated conjugates after administration (A) to tumor-bearing animals and (B) to non-tumor-bearing animals. Group 1 received CYT-0303-B72.3 conjugate (non-reduced); Group 2, CYT-0303-B72.3 conjugate reduced at pH=6.0; Group 3, CYT-0325-B72.3 conjugate; and Group 4, CYT-0324-B72.3 conjugate. See text for experimental details. Groups: 1 ▨▨ 0303; 2 ▨▨ R0303; 3 ▨▨ GY; and 4 ▭ IODO

DETAILED DESCRIPTION OF THE INVENTION

The present invention is directed to novel radiohalogenated compounds which are useful as intermediates for preparing radioactive glycoprotein conjugates in which the radiolabel is site specifically attached to an oxidized carbohydrate moiety of the glycoprotein molecule. When the glycoprotein is an antibody or antibody fragment, the oxidized carbohydrate moiety is not part of nor directly involved with the antigen binding site of the molecule. The radioactive antibody conjugates prepared using the radiohalogenated compounds of the invention retain substantially the same immunospecificity as the unconjugated antibody molecule.

The radiohalogenated compounds of the present invention comprise derivatives of activated aromatic compounds in which the aromatic ring is "activated" by the presence of an hydroxy, alkoxy or hydroxyalkoxy group located "para" to the radiohalogen. As used throughout the present specification, the term "activated aromatic compound" is intended to encompass an aromatic compound which contains a hydroxy, alkoxy or hydroxyalkoxy substituent. The activated aromatic compounds from which the radiohalogenated compounds are derived have a blocking group, such as an alkyl, hydroxyalkyl, ester, alkyl ester, an alkyl moiety substituted with a leaving group such as chloride, bromide, tosylate, etc. or an alkyl moiety substituted with a primary or secondary amino group located "ortho" to the activating group so that when the activated aromatic compound is radiohalogenated, the radiohalogen moiety is added at the "para" position and is not added at the "ortho" position. The radiohalogenated compounds of the invention thus avoid any inherent metabolic instability associated with radiohalogen substitution of the "ortho" position and when administered in vivo the radiohalogenated compounds of the invention are resistant to dehalogenation by dehalogenation enzymes.

Radiohalogenated Compounds

The radiohalogenated compounds of the invention are represented by the general formula:

in which:
R¹ = H, alkyl or hydroxyalkyl:

$R^2$ = acid hydrazide, alkyl acid hydrazine, hydrazino, alkylhydrazine, alkylphenylhydrazine, alkylamine or alkoxyamine;

$R^3$ = H, alkyl or $R^2$;

$R^4$ = alkyl, hydroxyalkyl or $R^2$; and

*X = is a radioisotope of a halogen selected from the group consisting of iodine, bromine, fluorine and astatine.

As used in the present specification, the term "alkyl" is intended to encompass straight or branched chain alkyl moieties having from 1–4 carbon atoms.

The radiohalogenated compounds of the present invention further comprise a reactive amine group which is available for reaction with an oxidized carbohydrate moiety of an antibody or antibody fragment to form a clinically useful site-specifically attached radiohalogenated antibody conjugate. As used in the present specification, the term "reactive amine" is intended to encompass an amine containing moiety which reacts with an aldehyde group with the expulsion of water to form a C==N bond. Thus a "reactive amine" includes but is not limited to hydrazino, hydrazide, phenylhydrazine, alkylhydrazine, alkoxyamine groups, etc.

Exemplary radiohalogenated compounds of the present invention include but are not limited to: 2-hydroxy-3-methyl-5-*halobenzoyl hydrazide; 2-hydroxy-3-(2,3-dihydroxypropyl)-5*halobenzoyl hydrazide; 2-(2,3-dihydroxy)propoxy-3-methyl-5-*halobenzoyl hydrazide; 2,-hydroxy-3,-methyl-5,-*halohydrocinnamoyl hydrazide; 2-hydroxy-3-methyl-5-*halo-α-aminotoluene; etc. in which *halo represents a radiohalogen moiety. Exemplary radioiodinated compounds include but are not limited to: 2-hydroxy-3-methyl-5-*iodobenzoyl hydrazide; 2-hydroxy-3-(2,3-dihydroxypropyl)-5-*iodobenzoyl hydrazide; 2-(2,3-dihydroxy)propoxy-3-methyl-5-*iodobenzoyl hydrazide; 2'hydroxy-3'-methyl-5'-*iodohydroxinnamoyl hydrazide; 2-hydroxy-3-methyl-5-*iodo-α-aminotoluene, etc., in which *iodo represents a radioactive iodine moiety such as I-123, I-125, I-131, etc.

Radiohalogen moieties which are useful according to the invention include any radioisotope of iodine, such as I-123, I-125, I-131, etc.; bromine such as Br-75, Br-76, Br-77; fluorine, such as F-18, and astatine, such as At-211. The particular radiohalogen is chosen according to the intended use of the radioactive conjugate desired. For in vivo diagnostic imaging applications using a gamma camera, I-123 and I-131 are preferred. For in vivo diagnostic imaging applications using positron tomographic imaging, F18, Br-75 and Br-76 are preferred. On the other hand, for in vitro applications including particularly radioimmunoassays, I-125 and I-131 are preferred. For in vivo therapeutic applications, preferred radiohalogens include I-131, Br-77 and At-211.

PREPARATION OF RADIOHALOGENATED COMPOUNDS

The radiohalogenated compounds of the invention are prepared according to the following reaction scheme:

An "activated" aromatic compound having a blocking group selected from the group consisting of alkyl, hydroxyalkyl, ester, alkyl ester, an alkyl moiety substituted with a leaving group such as chloride, bromide, tosylate, etc. and an alkyl moiety substituted with a primary or secondary amino group located ortho to the "activating" moiety is radiohalogenated to form an intermediate to which a reactive amine group is then attached according to reaction Scheme 1, 2, or 3 below to form a radiohalogenated compound of the present invention.

When the radiohalogen exists in ionic form, e.g., radioactive isotopes of iodide or bromide, radiohalogenation is accomplished by reacting the activated aromatic compound with a mixture of a radioactive and a non-radioactive salt of the halogen in an appropriate solvent in the presence of an oxidant, such as Cholamine-T; Iodobeads ™ (Pierce Chemical Company); Iodogen ™ (Pierce Chemical Company), etc. When the radiohalogen exists in molecular form, e.g., radioactive isotopes of fluorine or astatine, an oxidant is not necessary and the radiohalogenation is accomplished merely by reacting the activated aromatic compound with a mixture of radioactive and non-radioactive isotopes of the radiohalogen in appropriate solvent.

According to one embodiment of the invention, a reactive amine group is attached to a radiohalogenated intermediate using a displacement reaction according to the following scheme:

Scheme I in which

OR represents an ester moiety such as a methyl ester, an ethyl ester, an N-hydroxysuccinimide ester, etc.;

Z represents NH or NR in which R is $CH_3$, $CH_2CH_3$ or and n represents 0, 1, 2, 3 or 4.

In this embodiment, a radiohalogenated aromatic ester is dissolved in an appropriate solvent and reacted with at least one equivalent of a hydrazinolysis reagent, e.g. anhydrous hydrazine. Any solvent in which the ester is soluble but which does not react either with the ester or with the hydrazinolysis reagent is useful for this reaction. The mixture is stirred at room temperature until the starting materials are substantially reacted and the desired product is isolated, for instance, by removal of the solvent. The reactive amine group of the radiohalogenated compound formed which is available for site specific attachment to an oxidized carbohydrate moiety of an antibody molecule is an acid hydrazide or an alkyl acid hydrazide.

According to another embodiment of the invention, a reactive amine group is attached to a radiohalogenated intermediate using a diazotiazation reaction according to the following scheme:

Scheme II in which n represents 0, 1, 2, 3, or 4.

In this embodiment, a radiohalogenated intermediate containing a primary, amine in an aqueous acidic solution is reacted with at least an equivalent of a nitrosating agent such as nitrous acid. The resulting aqueous solution is then reacted with a reduring agent such as stannous chloride, etc. The desired radiohalogenated product is isolated from the aqueous solutior using conventional techniques such as acidification to form the desired hydrazine, precipitation or removal of the solvents. The reactive amine group of the radiohalogenated compound formed which is available for site specific attachment to an oxidized carbohydrate moiety of an antibody molecule is a hydrazine, an alkylhydrazine or an alkylphenylhydrazine.

According to yet another embodiment of the invention, a reactive amine group is attached to a radiohalogenated intermediate by a displacement reaction according to the following scheme:

SCHEME III

Y represents a leaving group such as a non-radioactive halogen moiety e.g., Cl, Br, etc., a tosylate group, etc.

Z represents NH or NR in which R is alkyl, OH or and n 0, 1, 2, 3 or 4.

In this embodiment, a radiohalogenated intermediate having a displaceable group such as a non-radioactive halogen, tosylate group, etc. is dissolved in an appropriate solvent and reacted with a hydrazinolysis reagent or a hydroxylamine. The reaction mixture is stirred at room temperature or heated until the reaction is substantially complete. The desired product is isolated for instance by removal of the solvents. The reactive amine group of the radiohalogenated compound formed which is available for site specific attachment to an oxidized carbohydrate moiety of an antibody molecule is a hydrazino, an alkylhydrazine, an alkylphenylhydrazine or an alkoxyamine.

In practice, the method of the invention according to Scheme I can be illustrated by an example in which 2-hydroxy-3-methyl-5-*iodobenzoyl hydrazide is formed as follows:

Methyl-2-hydroxy-3-methylbenzoate is added to approximately 1.1 equivalents of a mixture of sodium iodide and sodium 125-iodide dissolved in a sufficient amount of N,N-dimethylformamide to give a homogeneous solution. About 1.1 equivalents of Chloramine-T is introduced and the red-orange reaction mixture allowed to stand for two hours at room temperature. At least 1.5 equivalents of saturated sodium thiosulfate solution and a ten fold amount of water is added to the reaction vial. The resultant white slurry is poured onto a chromatography column and inorganic impurities are eluted by washing with water (about 10 ml). The desired product is eluted with 10 ml of methanol and four equivalents of anhydrous hydrazine is added to the methanolic fraction. This reaction solution is refluxed for about 18 h and then the solvents evaporated to yield the desired product.

The formation of the radiohalogenated compound can be monitored by thin layer chromatography (TLC) or high performance liquid chromatography (HPLC) and the desired compound can be purified by HPLC or column chromatography.

Site-Specifically Attached Conjugates

According to the invention, the radiohalogenated compounds are advantageously used to prepare site-specifically attached radioactive antibody conjugates. The radioactive antibody conjugates are prepared according to methods described in U.S. Pat. No. 4,671,958 issued to Rodwell et al. (see also, European Patent No. 85401776.1 published Mar. 26, 1986).

Briefly, a carbohydrate side chain of an antibody or antibody fragment which is not part of nor directly involved with or is located cutside the antigen binding region of the antibody, is selectively oxidized or enzymatically modified to form an aldehyde group. The resulting aldehyde is reacted with an amine group (e.g., ammonia derivatives such hydrazino groups, acid hydrazide, phenylhydrazine, alkylhydrazine, alkoxyamine, etc.) to form a hydrazone, phenylhydrazone, oxime or substituted derivative thereof and reduced forms thereof.

Chemical Methods of Oxidation

Oxidation of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, In Organic Reactions 2, p.341; Bunton, 1965, Oxidation in Organic Chemistry, Vol. 1 (Wibert, ed.), Academic Press, New York, p.367.

Oxidation of the antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, two to ten times as much as the amount of the oxidizable carbohydrate. The optimal amount, however, can be determined by routine experimentation.

In the process for oxidizing antibodies with oxygen acids or salts thereof, the optional ranges include a pH of from about 4 to 8, a temperature of from 0° to 37° C., and a reaction period of from about 15 minutes to 12 hours.

During the oxidation of the antibody with an oxygen acid or a salt thereof, light is preferably excluded to prevent over oxidation of the glycoprotein.

Enzymatic Methods of Oxidation

Oxidation of the carbohydrate portion of antibody molecules may also be done with the enzyme, galactose oxidase (Cooper et al., 1959, J. Biol. Chem.

234:445–448). The antibody is used in aqueous solution, the concentration being generally 0.5 to 10 mg/ml. The enzyme generally is used at about 5 to 100 units per ml of solution, at a pH ranging from about 5.5 to about 8.0. The influence of pH, substrate concentration, buffers and buffer concentration on enzyme reaction are reported in Cooper et al., supra.

Attachment

Antibody conjugates are produced by reacting the oxidized carbohydrate portion of an antibody or antibody fragment with a radiohalogenated compound having an available reactive amine group such as hydrazino, hydrazide, phenylhydrazine, alkylhydrazine, alkoxyamine, etc. The immediately resulting products contain a carbon-nitrogen double bond resulting from elimination of a molecule of water from the initial addition products:

antibody-CH=N—R + H$_2$O.

For a general discussion of the reaction of aldehydes with hydrazides, see March 1978, In Advanced Organic Chemistry: Reactions Mechanisms and Structure, McGraw Hill Co., New York, pp. 824–825.

A solution of the oxidized antibody at a concentration of from about 0.5 to 20 mg/ml is mixed with a radiohalogenated compound (molar ratios of reactive amine group to antibody aldehyde ranging from about 1 to about 10,000) and the solution incubated for from about 1 to 24 hours. Suitable temperatures are from 0° to 37° C. and pH may be from about 6 to 8.

After the antibody conjugates have been formed, they can optionally be stabilized with a suitable reducing agent, such as sodium cyanoborohydride or sodium borohydride. Reducing agent is generally added to a molar excess of from about 10 to 500 fold molar excess over available aldehyde groups, pH from about 4.0–6.5. For a general discussion, see Jentoft and Dearborn, 1979, J. Biol. Chem. 254:4359.

It has surprisingly been discovered that the biological half-life of the antibody conjugates can be controlled by varying the extent of reduction of the covalent bond formed between the reactive amine moiety of the radiohalogenated compound and the aldehyde moiety of the oxidized carbohydrate of the antibody. (See Section 7, infra). For example, reduction of the bond at pH of about 4.0–4.75 increases the biological half-life when compared to reduction at about pH=6.0 or no reduction at all. Depending upon the in vivo application, the antibody conjugates can advantageously be modified to yield conjugates with the desired biological half-life.

Antibodies

Antibodies direced against any determinant of any antigen or hapten may be used in the present invention. While both conventional polyclonal antibodies and monoclonal antibodies are suitable, monoclonal antibodies offer several advantages. Each monoclonal antibody is specific for one antigenic determinant. Additionally, a large amount of substantially homogenous monoclonal antibodies can be produced efficiently and economically using techniques known to those of skill in the art.

As used throughout the application, the term "antibody" is intended to encompass whole antibody molecules as well as any antibody fragments which contain a carbohydrate moiety which is not part of nor directly involved with the antigen binding region of the antibody molecule. Antibody fragments including, but not limited to half antibody molecules (a single heavy: light chain pair, Fab, Fab' or (Fab')$_2$ fragments can be used to prepare antibody conjugates.

In one embodiment of the invention, radiohalogenated antibody fragment conjugates can be prepared by reacting a soluble radiohalogenated conjugate of the invention with an activated thiol protease enzyme to form an antibody (Fab')$_2$ radiohalogenated compound conjugate as described in U.S. Patent Application Ser. No. 152,209, incorporated herein by reference.

In another embodiment of the invention, antibodies having an increased number of mannose moieties available for site specific covalent attachment can be used according to the reaction scheme. Conjugates formed using these "high mannose" antibodies may have higher specific radioactivity due to the higher number of sites available for covalent attachment of a radiohalogenated compound. "High mannose" antibodies are described in copending U.S. Patent Application Ser. No. 153,175 which is incorporated herein by reference.

Classes of antibodies including IgG, IgM, and IgA can be used in the method of the present invention.

As stated above, antibodies directed against any determinant of any antigen or hapten can be employed in the reaction scheme described herein. Such determinants include, but are not limited to determinants of: tumor and malignant cells, bacterial, fungal, viral, parasitic, mycoplasmal, histocompatability, differentiation and other cell membrane antigens, pathogen surface antigens, toxins, enzymes, allergens, drugs, any biologically active molecules, etc. In some instances, a combination of monoclonal antibodies reactive with different antigenic determinants can be used.

Applications

The radiohalcgenated antibody conjugates of the present invention are advantageously useful for a variety of in vivo therapeutic and diagnostic applications as well as for in vitro diagnostic applications.

According to one embodiment of the invention, the antibody conjugates are employed for in vivo applications. In this embodiment, the radiohalogenated antibody conjugates possess aqueous solubility such that they are suitable for in vivo administration. The properties of the antibody moiety in being immunospecific for and immunoreactive with a particular antigen or antigenic determinant associated with a cellular disorder render the compositions ideally suited for delivery of a therapeutic or diagnostic agent to specific cells, tissues, or organs or any other in vivo site having that antigenic determinant. The properties of the radiohalogenated compound moiety of the present antibody conjugates in resisting de-halogenation by in vivo dehalogenation enzymes render the compositions ideally suited for in vivo use without the undesirable accumulation of the free radiohalogen to non-target tissues including particularly the thyroid. Thus, the properties of the present radiohalogenated antibody conjugates in having superior biodistribution to an intended target site and not to non-target sites including especially liver and spleen and not to the thyroid (see Section 7, infra) compared to conventionally prepared radiohalogenated antibody conjugates render the present compositions especially suited for in vivo delivery of a therapeutic or diagnostic radioisotope when persistence of the agent at the target site is desired.

Additionally, as explained in Section 5.3, supra, the present antibody conjugates can be stabilized by treatment with a suitable reducing agent. It has been discovered that the biological half-life of the resultant conjugate can be controlled by controlling the extent of reduction of the covalent bond between the oxidized carbohydrate moiety of the antibody and the reactive amine moiety of the radiohalogenated compound, for example, by selection of the pH of the reduction conditions. (See Section 7, infra). Thus, surprisingly use of the present conjugates may afford a means for controlling the biological half-life of a therapeutic or diagnostic conjugate administered in vivo. Depending upon the intended application, such control may be particularly important. For instance, in imaging a site of a thrombosis or blood clot, it may be desirable to achieve faster clearance of the blood pool and hence a shorter biological half-life would be desirable. This can be achieved by not reducing the covalent bond between the radiohalogenated compound and the antibody moiety. On the other hand, for therapeutic applications, a faster or slower clearance may be desired depending upon a number of variables including such as the dose regimen, the physical half-life of the radioisotope, etc. Adjustment of the biological half-life or clearance can be achieved by varying the extent (or non-extent) of reduction of the covalent bond in the present antibody conjugates.

In vivo administration may involve use of a therapeutically effective composition or a diagnostic composition comprising an aqueous soluble radiohalogenated antibody conjugate in any suitable carrier, including serum or physiological saline, with or without another protein, such as human serum albumin. Dosages of the antibody conjugates can be readily determined by one of ordinary skill and may differ depending upon the nature of the radiohalogenated compound attached and the intended purpose of the conjugate.

The route of administration is generally parenteral, with administration via an intravenous route generally preferred.

As used in this application the term "cellular disorder" is intended to include all neoplasms, such as cancers, adenomas, hyperplasias, etc.; certain immunological disorders, including graft-versus-host diseases (e.g., after bone marrow transplantation); immune suppressive disorders, (e.g., acquired immune deficiency syndrome (AIDS), after kidney or bone marrow transplantation); cardiovascular diseases such as those associated with the formation of atherloscelortic plaques, etc,; infections induced by viral, bacterial, fungal, mycoplasmal, or parasitic agents, etc.

Therapeutic applications generally involve treatment of a cellular disorder by administering an effective amount of a radiohalogenated antibody conjugate in which the radiohalogen is a therapeutic agent. Preferred therapeutically effective radiohalogens include I-131, Br-77 and At-211.

Diagnostic applications generally involve imaging of specific tissues or a cellular disorder by administration of a sufficient amount of an aqueous soluble antibody radiohalogenated conjugate to enable detection or localization of the conjugate at the target tissue in an appropriate time frame. For diagnostic purposes, the radiohalogenated compound attached to the antibody contains a radioactive isotope that can be detected using an imaging device. A variety of radiohalogenated moieties are suited for preparing conjugates for imaging purposes. Radioisotopes such as I-123 and I-131 are preferred for imaging using a gamma camera for detection. Positron emitting radiohalogens such as F-18, Br-74 and Br-76 are preferred for imaging using positron tomographic imaging.

Tissues and cellular disorders which may be imaged include any solid neoplasms, certain organs such as lymph nodes, parathyroids, spleen and kidney, sites of inflamation or infection (e.g. macrophages at such sites), mycocardial infarction or thromboses, (neoantigenic determinants or fibrin, platelets), etc.

According to another embodiment of the invention, the antibody conjugates are employed for in vitro applications. In this embodiment, the radiohalogenated antibody conjugate may be soluble in aqueous solutions or alternatively may be immobilized by attachment to a solid, insoluble support such as a plate, a bead, etc. The radiohalogenated antibody conjugates are advantageously used in a variety of in vitro assays to detect antigens or antigenic determinants of tumor and malignant cells, bacterial, fungal, viral, parasitic, mycoplasmal, histocompatability, differentiation and other cell membrane antigens, pathogen surface antigens, toxins, enzymes, allergens, drugs, any biologically active molecules, etc. For in vitro applications, radiohalogens such as I-125 and I-131 are preferred.

The following non-limiting examples serve to further illustrate the invention and are in no way intended as a limitation thereon.

PREPARATION OF 2-HYDROXY-3 METHYL-5-*IODOBENZOYL HYDRAZIDE (CYT-0303)

CYT-0303 having the formula in which *I represents I-125 was prepared according to the present invention as follows:

The activated aromatic ester methyl-2-hydroxy-3-methylbenzoate (CYT-0299,1) was radioiodinated forming the intermediate methyl-2-hydroxy-5-iodo-3-methylbenzoate (CYT-0300,3), which was subsequently hydrazinolysed yielding CYT-0303. The reaction scheme is represented:

-continued

In practice, a 10 ml round bottom flask was charged with 12.0 mg of 1, 0.5 ml of N,N-dimethylformamide (DMF), 14.2 mCi of Na-I-125 solution (Amersham Corp., Arlington Hts, IL) and 20.2 mg of Chloramine-T (Aldrich, Milwaukee, WI, 2). The reaction mixture was incubated at room temperature for about 15 minutes with stirring. Then 10.8 gm of NaI (0.072 m moles) was added and the mixture incubated at room temperature for about 1.75 h. Any excess molecular iodine was quenched by adding 2.0 ml of saturated aqueous sodium thiosulfate solution and the resultant white slurry was poured onto an RP-18 extraction cartridge (J.T. Baker Chemical Company, Phillipsburg). The inorganic impurities were flushed from the cartridge with 10.0 ml of water, and the desired intermediate CYT-0300 (3) was eluted using 15.0 ml of methanol. Then, 0.4 ml of anhydrous hydrazine ($NH_2NH_2$) was added to the methanolic fraction and the clear, colorless reaction mixture was refluxed at about 60° C. for 18 h. The solvents were evaporated yielding a white residue. The residue was washed with 3.0 ml of water in three 1.0 ml portions to yield 9.78 mCi CYT-0303 (3) having a specific radioactivity of about 164 μCi/μmole. On TLC/50% ethylacetate/hexane, $K_5f$ silica gel, short wave UV visualization: Rf, 0.2.

SUPERIOR BIODISTRIBUTION OF CYT-0303-ANTIBODY CONJUGATES

The following experiments demonstrate that a radioiodinated antibody conjugate prepared using a radioiodinated compound of the present invention site-specifically attached to an oxidized carbohydrate moiety of an antibody molecule exhibited superior biodistribution when administered in vivo to experimental animals in comparison with analogous conjugates prepared either (a) using a similarly site specifically attached radioiodinated compound having an "ortho" iodine moiety, or (b) using a radioiodinated compound that was non-specifically or randomly attached to the antibody molecule.

Preparation of a Radioiodinated Compounds for Comparison

Two radioiodinated compounds, i.e. 3,5-diiodoglycyl-L-tyrosine (CYT-0325) having an amine group suitable for site-specific covalent attachment to an oxidized carbohydrate moiety of an antibody and an "ortho" iodine group; and 5-iodo-3-methylsalicylic acid, N-hydroxysuccinimide ester (CYT-0324) having a reactive carboxyl group for non-specific or random attachment to an amine group of an antibody were prepared as set forth below.

Preparation of 3,5-*Diiodoglycyl-L-Tyrosine (CYT-0325)

CYT-0325 having the formula:

was prepared according to the following reaction scheme:

In practice, a 10. ml round bottom flask was charged with 0.01 gm of glycyl-L-tyrosine hydrate (Sigma Chemical Co., St. Louis, MO., 4), 1.0 ml of PBS buffer pH=7.4, 0.015 gm of sodium iodide and 5.13 mCi of NaI-125. (Amersham Corp.). The reaction mixture was stirred rapidly at room temperature until a clear, homogenous mixture was obtained. Then 0.022 g of 2 (Aldrich, Milwaukee, WI) was added in one portion. The resultant orange-red mixture was incubated at room temperature for 1.5 h with stirring. Saturated aqueous sodium thiosulfate solution (0.5 ml) was then added and the solvents distilled off at reduced presure, leaving a white waxy residue. The waxy residue was then eluted through an RP-18 chromatography cartidge (J.T. Baker Chemical Company, Phillipsburg, NJ) using 10.0 ml of water followed by 10.0 ml of methanol. The solvent was evaporated from the methanolic fraction leaving CYT-0325 as a white waxy solid. Yield: 0.020 gm (5.1 mCi having a specific radioactivity of 124 μCi/μmole.

Preparation of 5-*IODO-3-Methylsalicyclic Acid, N-Hydroxysuccinimide Ester (CYT-0324)

CYT-0324 having the formula:

was prepared by radioiodination of 3-methylsalicylic acid, N-hydroxysuccinide ester (CYT-0323). CYT-0323 having the formula:

was prepared according to the following reaction scheme:

In practice, a 200 ml round bottom flask was charged with 22.67 gm of 3-methylsalicylic acid (Aldrich Chemical, Milwaukee, WI, 5), 50.0 ml of ethylene glycol dimethyl ether and 17.15 gm of N-hydroxysuccinimide (6), and the mixture was cooled to about 0° C. Then 30.75 gm of 1,3-dicyclohexylcarbodiimide (7) dissolved in 50.0 ml of ethylene glycol dimethyl ether was added to the cold reaction mixture. The reaction mixture was removed from the cooling bath and the internal temperature was allowed to slowly rise to about 20°–25° C. The resulting white slurry was stirred for about 72 h at room temperature; and then filtered to remove any precipitate which formed. The filtrate was evaporated under reduced pressure to yield a yellow-white solid residue The yellow-white residue was dissolved in 150.00 ml of hot isopropyl alcohol, the solution was cooled to about 20°–25° C. and allowed to stand at room temperature for about 18 h. The precipitated CYT-0323 was obtained as a white solid by filtration and drying the filter cake at 40° C. at 30 mm Hg pressure. Yield: 33.39 gm (90%). On TLC: 50% ethyl acetate/hexane, K₅f silica gel, short wave UV visualization: Rf 0.6.

CYT-0324 was then prepared according to the following reaction scheme:

In practice, a 10 ml round bottom flask was charged with 10.0 mg of CYT-0323, 1.0 ml of PBS Buffer, pH=7.4, 2.0 ml acetonitrile (CH₃CN) and 8.0 mg of sodium iodide plus 3.35 mCi of Na-I-125 (Amersham Corp., Arlington Hts, IL). When a homogeneous solution was obtained, 11.4 mg of Chloramine-T was added. The reaction mixture was allowed to stand at room temperature for about 1.5 h with occasional stirring. Then, any unreacted molecular iodine was quenched by adding 1.0 ml of saturated aqueous sodium thiosulfate. The desired CYT-0324 product was eluted from the extraction cartridge with 10 ml of methanol. The solvents were incorporated from the methanolic fraction, yielding about 5.0 mg (1.1 mCi) of CYT-0324 having a specific radioactivity of about 82.7 µCi/µ mole. On TLC: 50% ethyl acetate/hexane, Em-60 silica gel (EM Science, Cherry Hill, Rahway, NJ), short wave UV visualization: Rf, 0.56.

Preparation of Antibody Conjugates

The antibody employed in these experiments was a murine monoclonal antibody reactive with human breast and colon cancer obtained from hybridoma cell line ATCC No. B72.3 (hereinafter "B72.3 antibody") described in U.S. Pat. No. 4,522,918 issued to Schlom et al. (See, Nuti et al., 1982, Int. J. Cancer 29:539-45). The B72.3 antibody is reactive with an antigen found on a number of cancerous cells, including LS174T cells (ATCC) human colon adenocarcinoma cells.

Site-Specific CYT-0303 Conjugates

A number of CYT-0303-B72.3 conjugates were prepared in which CYT-0303 was site specifically attached to an oxidized carbohydrate moeity of the B72.3 antibody. The carbohydrate moiety of the B72.3 antibody was first oxidized by reacting an aliquot of the antibody with 10 mM sodium periodate (NaIO₄), 1500–5000 fold molar excess, in the dark for 1 h in PBS buffer, pH=6.0. The oxidized antibody was then desalted on an NAP-25 column using phosphate buffered saline (PBS) buffer. The CYT-0303 was attached to the oxidized carbohydrate moiety of the antibody by reacting a 20 fold molar excess of CYT-0303 with the antibody in acetate buffered saline, pH=5.0 containing sufficient DMF (about 10-20%) to obtain a homogeneous solution. The conjugation reaction was allowed to proceed for about 5-8 h at room temperature. All conjugates were purified using a TSK-3000 high performance liquid chromatography column eluted with PBS, pH=7.4, to remove any aggregates that may have formed.

In some instances, the hydrazone linkage forming the site-specific attachment between the CYT-0303 and the oxidized carbohydrate of the antibody in the conjugates was reduced by reaction with sodium cyanoborohydride (NaCNBH₃). The NaCNBH₃ was added in about 4000 molar excess to the oxidized B72.3 antibody and CYT-0303 in acetate buffered saline, at pH 4.5–6.0, and the reaction mixture allowed to incubate overnight at 4° C. The reduced conjugate was then purified using a TSK-3000 HPLC column eluted with PBS at pH =7.4 to remove any aggregates that may have formed.

Site-Specific CYT-0325 Conjugates

CYT-0325-B72.3 conjugates were prepared in which CYT-0325 was site specifically attached to an oxidized carbohydrate of the B72.3 antibody as described above in Section 7.2.1. These conjugates differ significantly from those described in Section 7.2.1 in that there is an iodine substituent "ortho" to the hydroxy group of the phenolic region of the CYT-0325.

CYT-0325 was coupled to the oxidized carbohydrate moiety of B72.3 antibody (after desalting on NAP-25 column) by reacting the antibody with CYT-0325 at about 1000 to 1 molar excess in PBS buffer, at pH=6.0 containing about 2000 molar equivalents of $NaCNBH_3$. The incubation was allowed to proceed at 4° C. overnight and the resulting conjugate was purified by elution through a TSK-3000 HPLC column using PBS buffer at pH=7.4 to remove any aggregates that may have formed.

Non-Site Specific CYT-0324 Conjugates

CYT-0324-B72.3 conjugates were prepared in which a carboxyl group of the NHS ester moiety of CYT-0324 was randomly or non-site specifically attached to an amine of the antibody molecule as follows:

CYT-0324 (3 mg, 8.4 μmoles) was suspended in 0.4 ml of DMF and 0.6 ml of PBS (pH=7.4). B72.3 antibody (3.4 mg in 650 μl PBS, pH=7.4) was added to 55 μl of the CYT-0324/DMF suspension (about 0.165 mg CYT-0324) forming a reaction mixture containing about 20-fold molar excess CYT-0324 to antibody. The reaction mixture was incubated for 1 h at 4° C.; then about 40 molar excess glycine was added to consume any unreacted CYT-0324. The non-site specifically attached CYT-0324-B72.3 conjugate was purified by elution through a NAP-10 column using PBS buffer, pH=7.4 to remove aggregates that may have formed.

In Vivo Biodistribution

A series of in vivo experiments were performed in order to compare the biodistribution of the CYT-0303 conjugates of the invention with analogous CYT-0324 conjugates, and CYT-0325 conjugates as well as with B72.3 antibody directly radioiodinated with Iodobeads TM following administration to animals bearing tumor xenografts having the target antigen for which the B72.3 antibody is specific. In each series of experiments, a group of non-tumor "normal" animals served as controls. All animals were maintained on filtered water and Purina Laboratory Rodent Chow #5010, ad libitum.

In vivo experiments were conducted as follows. Briefly, tumor-bearing animals were obtained by subcutaneous injection of nu/nu Swiss mice (Taconic Farms, Germantown, NY) (6 weeks-6 months old; 18–30 gm) with $10^5$ LS1747 human colon adenocarcinoma cells (0.2 ml). All injections were made in the left rear flank. When tumors were palpable, i.e. about 10–15 mm ×15–20 mm in size, the experimental animals were divided into an appropriate number of groups of 4 animals each. Control "normal" Swiss or Balb c mice (Taconic Farms, Germantown, NY) were also divided into similar groups of 3 animals each. All experimental and "control" animals then received a measured aliquot of the appropriate I-125-radioiodinated - B72.3 conjugate (Day 0). The radioactivity in the animals was measured using a dose calibrator immediately after injection and for three days on a daily basis. On Day 3, the animals were sacrificed, weighed, and organs dissected to determine the level of radioactivity in a variety of tissues. Immediately prior to dissection, a sample of blood was collected. Radioactivity in all tissue samples was measured using the dose calibrator.

In one in vivo experiment, the biological half-life of the following radioiodinated B72.3 conjugates was directly compared: (1) CYT-0303-B72.3 in which the hydrazone bond was not reduced; (2) CYT-0303-B72.3 in which the hydrazone bond was reduced using $NaCNBH_4$ at pH=6.0, i.e. partially reduced; (3) CYT-0303-B72.3 in which the hydrazone bond was reduced using $NaCNBH_4$ at pH=4.75 i.e., substantially reduced; and (4) B72.3 antibody radioiodinated directly using Iodobeads TM according to the method of Colcher et al. (1984, Cancer Res. 44:5744-51) except that Iodobeads TM (Pierce Chemical Company, Rockford, IL) was used instead of Iodogen TM. Results obtained are presented in FIGS. 1–3.

Figure 1:
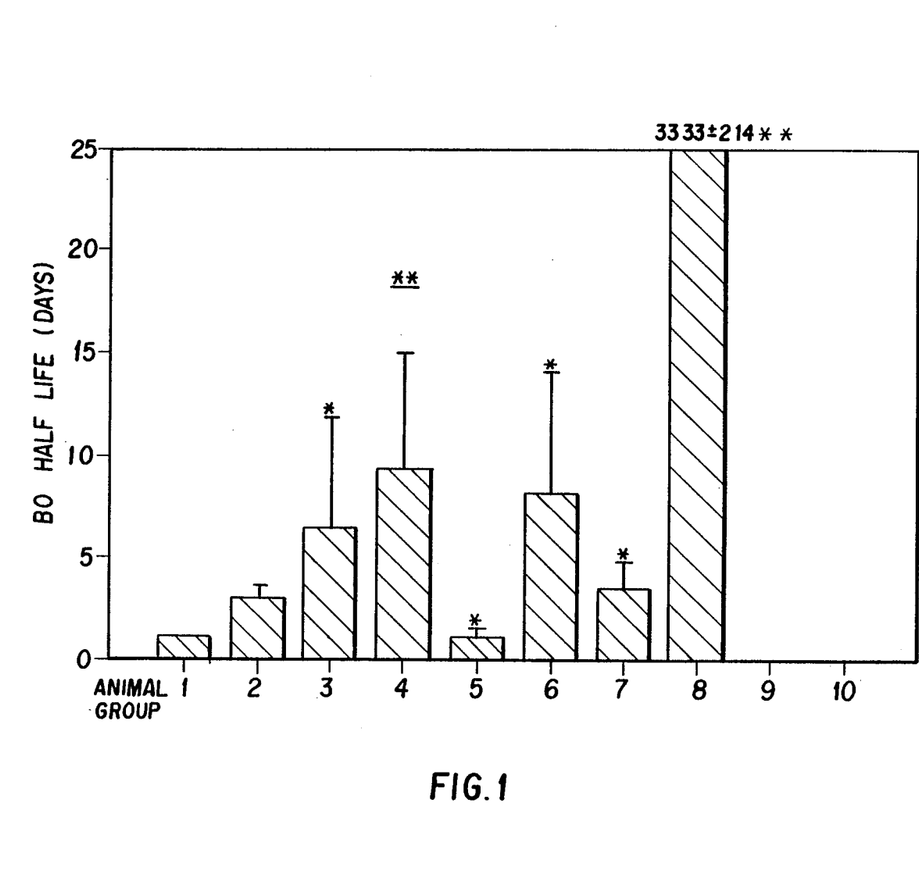
FIG. 1 represents the biological half-life (days) of radioiodinated antibody conjugates after administration to tumor-bearing and non-tumor-bearing animals: Groups 1 and 5 received CYT-0303-B72.3 conjugate; Groups 2 and 4, CYT-0303-B72.3conjugate treated with NaCNBH₄ at pH=6.0; Groups 3 and 6, CYT-0303-B72.3 conjugate treated with NaCNBH₄ at pH=4.75; and Groups: 4 and 8, B72.3 antibody directly radioiodinated using Iodobeads TM. See text for experimental details.

As shown in FIG. 1, the biological half-life of the non-reduced CYT-0303-B72.3 conjugate was significantly less than that of the directly radioiodinated B72.3 antibody when administered to either tumor-bearing (Group 1 vs Group 4) or non-tumor-bearing (Group 5 vs Group 8) animals. On the other hand, reduction of the hydrazone bond in the CYT-0303-B72.3 conjugate under, respectively pH =6.0 (Group 2) and under pH=4.75 (Group 3) apparently increased the biological half-life from about 1 day to about 3 days and 7 days, i.e., not significantly different from that of the directly radioiodinated B72.3 antibody when administered to tumor-bearing animals (compared with Group 4). Thus, it is apparent that control of the extent of reduction of the covalent bond formed between the amine group of the radiohalogenated compound and the oxidized carbohydrate moiety of the antibody permits control of the biological half-life of the conjugate when administered in vivo.

Figure 2:
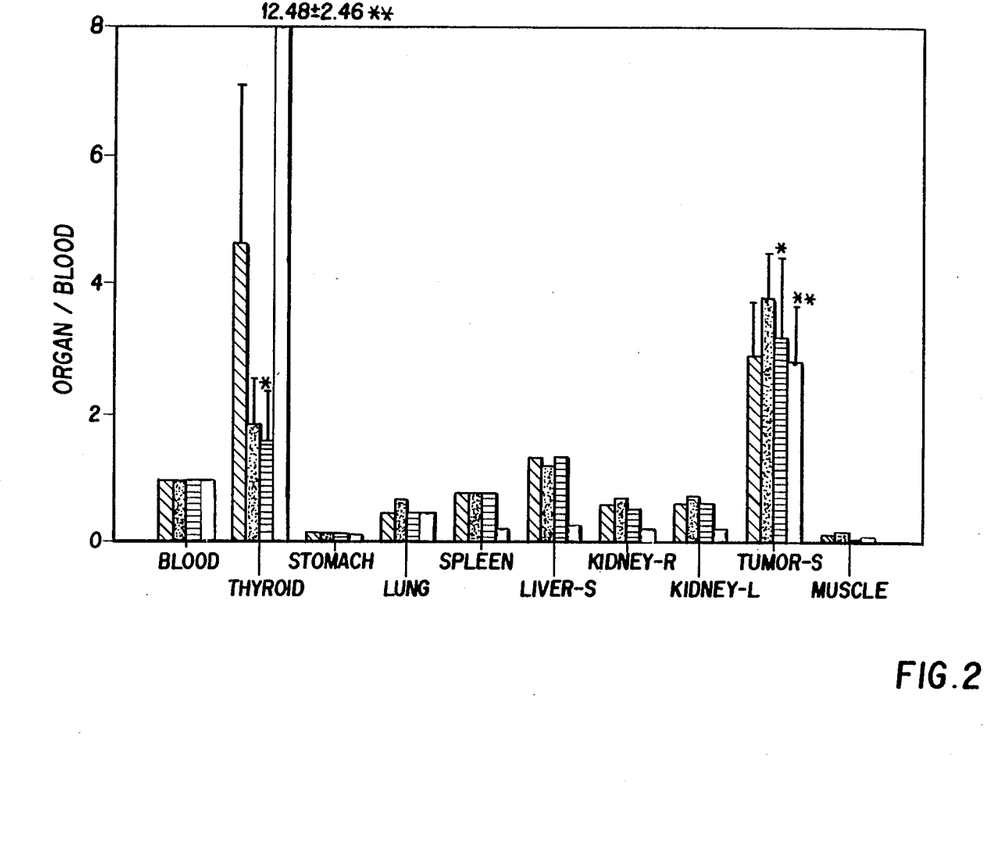
FIG. 2 represents the biodistribution, expressed as an organ/blood ratio, of the radioiodonated conjugates after administration to tumor-bearing animals. Groups 1–4 are the same tumor-bearing animals as shown in FIG. 1. Groups: 1 ▨▨ 0303; 2 ▨▨ R6-0303; 3 ▨▨; R4.75-0303 and 4 ▭ IODO IODO.
Figure 3:
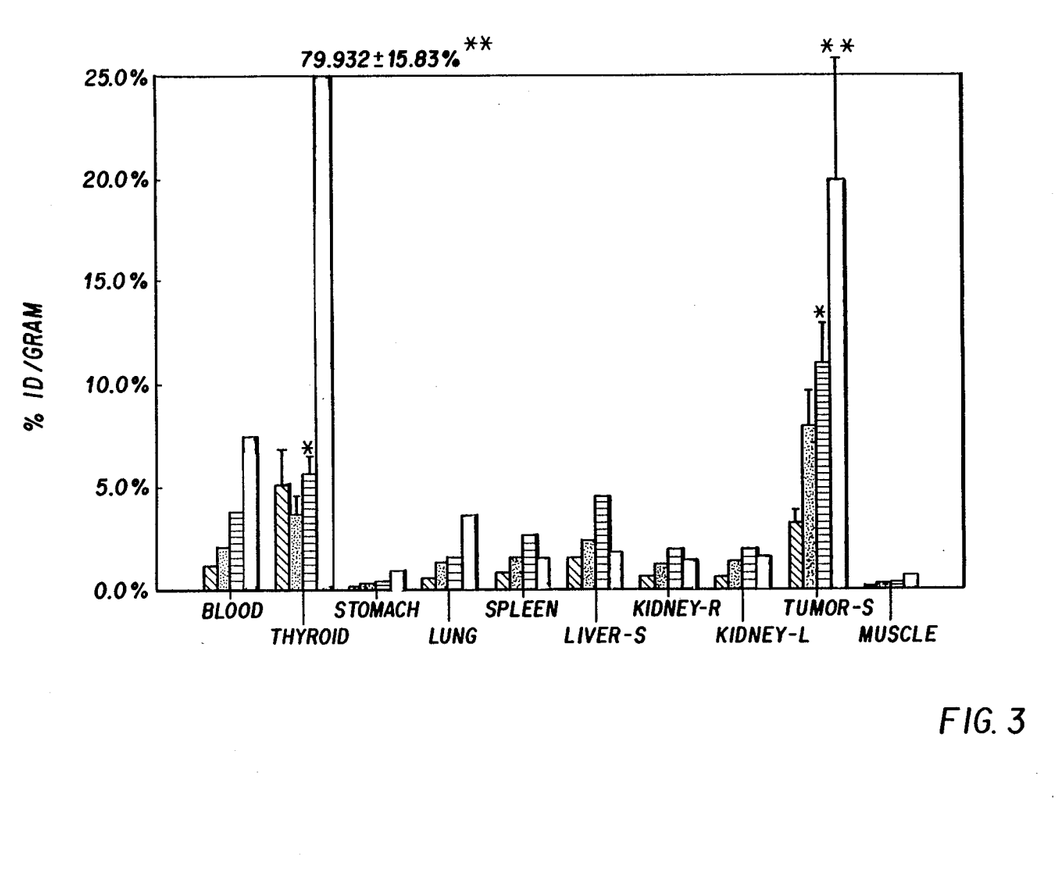
FIG. 3 represents the biodistribution, expressed as a percentage of the injected dose per gram (% ID/GRAM), of the radioiodinated conjugates. Groups 1-4 are the same tumorbearing animals as shown in FIGS. 1 and 2. Groups: 1 ▨▨ 0303; 2 ▨▨ R6-0303; 3 ▨▨ R4.75-0303 and 4 ▭ IODO IODO.

Additionally, in the same experiment, although the tumor/blood ratio of all four conjugates examined was substantially the same, the thyroid/blood ratio of the directly radioiodinated B72.3 antibody was about 7 times that of the CYT-0303-B72.3 conjugates which had been reduced either at pH=6.0 or at pH=4.75. (FIG. 2). Moreover, as shown in FIG. 3, although the percentage of the injected dose per gm (% ID/GRAM) of tumor of the directly radioiodinated B72.3 antibody was about 2 times that of the CYT-0303-B72.3 conjugate (reduced at pH=4.75), the percent of radioiodine in the thyroid of animals receiving the CYT-0303-B72.3 conjugate was only about 1/16 of that observed in animals receiving the conventionally radioiodinated antibody.

Thus, it is apparent that the site-specifically attached CYT-0303 conjugate of the present invention exhibits clearly advantageous delivery to a tumor site with substantially less loss of radioiodine to the non-target thyroid site when compared to conventionally directly radioiodinated target specific antibody. It appears that less dehalogenation occurred using the radiohalogenated conjugate of the invention when administered in vivo.

Figure 4A:
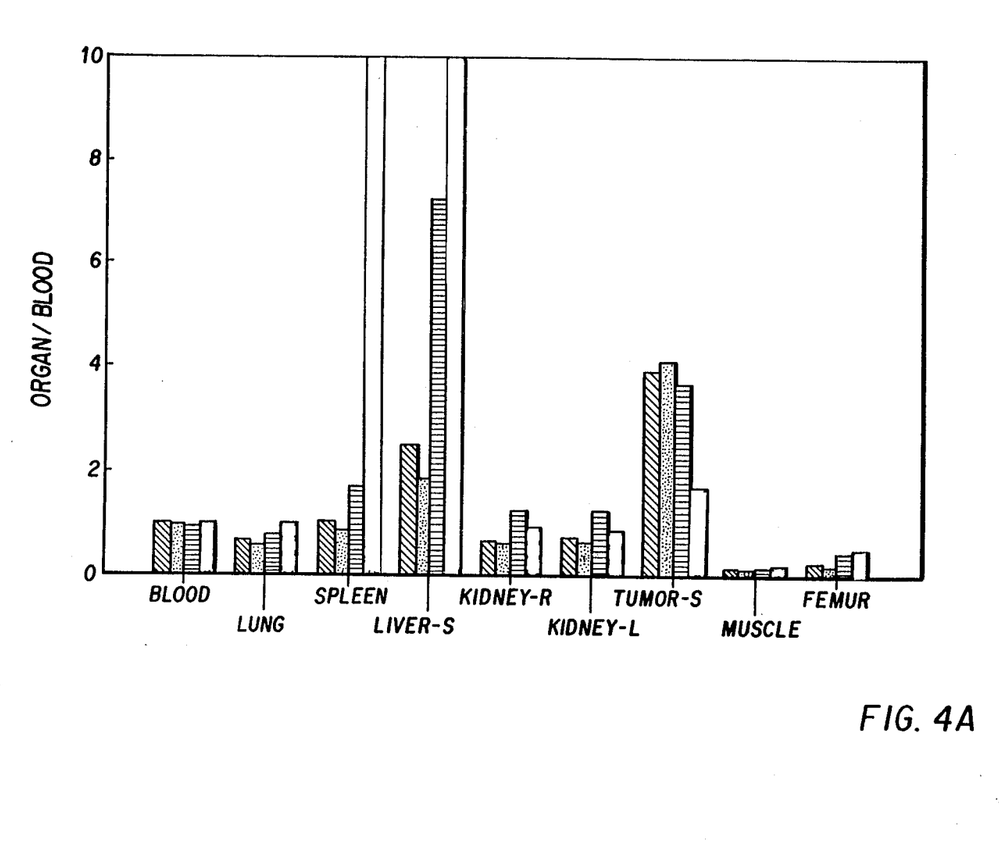
Figure 4B:
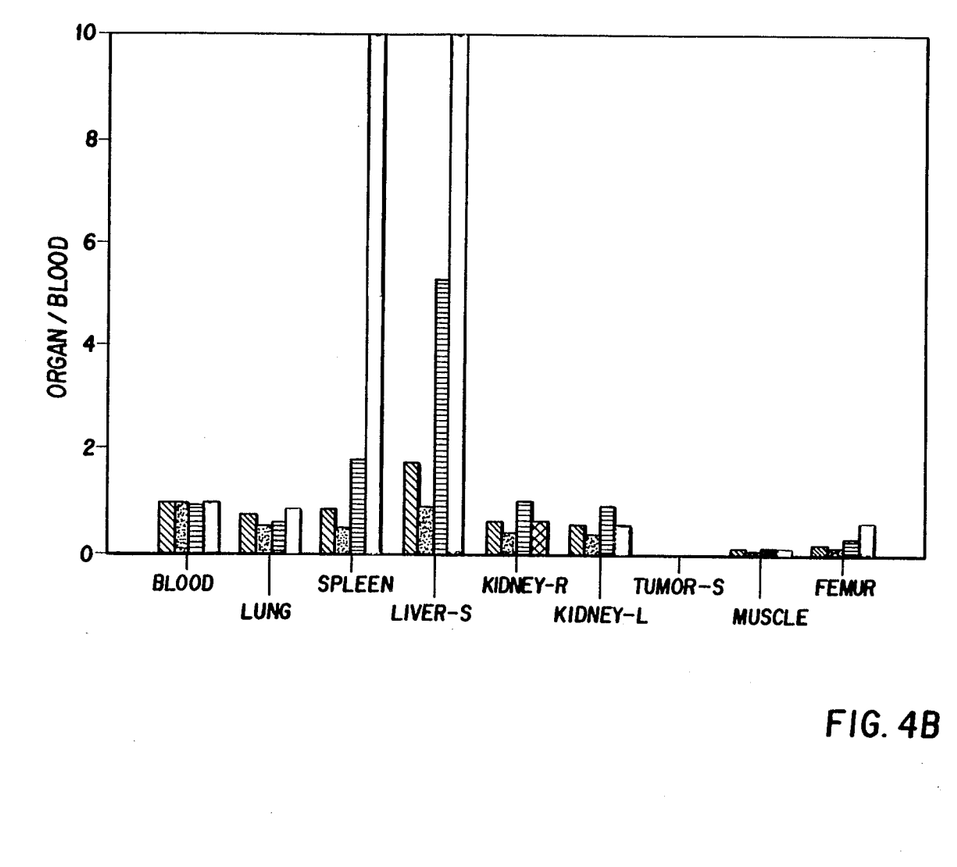

In another experiment, the biodistribution of the following radioiodinated antibody conjugates was compared as described above: (1) CYT-0303-B72.3 (non-reduced); (2) CYT-0303-B72.3 reduced with NaCNBH₄ at pH=6.0; (3) CYT-0325-B72.3; and (4) CYT-0324-B72.3. Results are presented in FIG. 4 (A and B) for tumor-bearing and non-tumor bearing animals, respectively.

As clearly demonstrated in FIG. 4 (A and B), although the organ/blood ratio of radiolabeled antibody conjugate was essentially the same in animals which received the site-specifically attached conjugates according to the present invention (Groups 1 and 2) and those which received the site-specifically attached CYT-0325 conjugate having an "ortho" iodine moiety (Group 3) and the non-site specifically attached CYT-0324 conjugate (Group 4), there was a significant difference in the distribution of the radiolabel to target tumor tissue and to non-target tissues, particularly the liver and spleen in animals in Groups 1-3 compared to animals in Group 4. As shown in FIG. 4A, in tumor-bearing animals the organ/blood ratio in the tumor was about 2 times greater in animals which received site-specifically attached conjugates (Groups 1-3) compared to those which received non-specifically attached conjugate (Group 4).

On the other hand, FIG. 4(A and B) shows that for both tumor-bearing and non-tumor-bearing animals, the organ/blood ratio of the non-target spleen was about 5 times greater in animals which received non-specifically attached conjugate (Group 4) compared to these which received site-specifically attached conjugates (Groups 1-3). Similarly, FIG. 4 (A and B) shows that undesirable delivery of radiolabel to non-target liver was about 5 times greater in animals which received non-site specifically attached conjugates (Group 4) compared to those which received site-specific conjugates of the invention (Groups 1 and 2). Of animals receiving the site-specifically attached conjugates only Group 3 which received a conjugate which unlike the conjugates of the invention had an "ortho" iodine moiety showed a substantial delivery of radiolabel to the liver. This may represent radiolabel which was dehalogenated and no longer attached to the antibody conjugate. In fact, the liver/blood ratio of the CYT-0325 conjugate and the CYT-0324 conjugate were about 4 times and 5.5 times greater than that of the CYT-0303 conjugates (both non-reduced and reduced), respectively. Additionally, the spleen/blood ratio of the CYT-0325 conjugate was about 3 times that of the CYT-0303 conjugates.

In summary, it is clear that when administered in vivo, the site-specifically attached conjugates of the present invention are delivered to an intended target site as well as or better than conventionally radioiodinated conjugates, and are not delivered to non-target sites such as liver and spleen. Moreover, in contrast to directly radioiodinated antibody which is significantly dehalogenated, the present radioiodinated antibody conjugates which do not have an ortho"iodine moiety, are not significantly dehalogenated when administered in vivo. Hence, the in vivo experiments demonstrate that the conjugates of the invention represent superior products for targeted in vivo delivery.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of the formula:

in which
$R^1$=H, alkyl or hydroxyalkyl;
$R^2$=acid hydrazide, alkyl acid hydrazide, hydrazino, alkylhydrazine, alkylphenylhydrazine, alkylamine or alkoxyamine;
$R^3$=H, alkyl or $R^2$;
$R^4$=alkyl, hydroxyalkyl or $R^2$; and
*=X a radioactive isotope of iodine, bromine, fluorine or astatine.

2. The compound according to claim 1, in which *X is selected from the group consisting of Iodine-123, Iodine-125, Iodine-131, Bromine-75, Bromine-76, Bromine-77, Fluorine-18, and Astatine-211.

3. The compound according to claim 1, which is selected from the group consisting of 2-hydroxy-3-methyl-5-*iodobenzoyl hydrazide; 2-hydroxy-3-(2,3-dihydroxypropyl)-*iodobenzoyl hydrazide; 2-(2,3-dihydroxypropoxy-3-methyl-5-*iodobenzoyl hydrazide; 2'-hydroxy-3'-methyl-5'*iodohydrocinnamoyl hydrazide; and 2-hydroxy-3-methyl-5-*iodo-α-aminotoluene in which * represents a radioactive iodo substituent.

4. 2-Hydroxy-3-methyl-5-*iodobenzoyl hydrazide, in which * represents a radioactive iodo substituent.

* * * * *